United States Patent
Krivitski et al.

(10) Patent No.: US 11,439,735 B2
(45) Date of Patent: Sep. 13, 2022

(54) METHOD AND APPARATUS FOR ASSESSING CARDIAC OUTPUT IN VENO-VENOUS EXTRACORPOREAL BLOOD OXYGENATION

(71) Applicant: Transonic Systems Inc., Ithaca, NY (US)

(72) Inventors: Nikolai M. Krivitski, Ithaca, NY (US); Gregory Galyanov, Ithaca, NY (US)

(73) Assignee: Transonic Systems Inc., Ithaca, NY (US)

( * ) Notice: Subject to any disclaimer, the term of this patent is extended or adjusted under 35 U.S.C. 154(b) by 251 days.

(21) Appl. No.: 16/752,035

(22) Filed: Jan. 24, 2020

(65) Prior Publication Data

US 2020/0237989 A1 Jul. 30, 2020

Related U.S. Application Data (60) Provisional application No. 62/796,800, filed on Jan. 25, 2019.

(51) Int. Cl.
*A61M 1/16* (2006.01)
*A61B 5/145* (2006.01)
*A61B 5/029* (2006.01)

(52) U.S. Cl.
CPC ........ *A61M 1/1607* (2014.02); *A61B 5/029* (2013.01); *A61B 5/14525* (2013.01);
(Continued)

(58) Field of Classification Search
CPC .... A61M 1/16; A61M 1/1603; A61M 1/1607; A61M 1/1615; A61M 1/1698;
(Continued)

(56) References Cited

U.S. PATENT DOCUMENTS

| | | | | |
|---|---|---|---|---|
| 5,685,989 A | * | 11/1997 | Krivitski | ............. A61M 1/3658 |
| | | | | 210/103 |
| 6,155,984 A | * | 12/2000 | Krivitski | ................ A61B 5/026 |
| | | | | 600/526 |

(Continued)

FOREIGN PATENT DOCUMENTS

| | | |
|---|---|---|
| WO | 2006096758 A2 | 9/2006 |
| WO | 2006096758 A3 | 9/2006 |

OTHER PUBLICATIONS

European Patent Office, Extended European Search Report issued in corresponding European Patent Application No. 20744707.9, dated Apr. 7, 2022.

(Continued)

*Primary Examiner* — Philip R Wiest
(74) *Attorney, Agent, or Firm* — Brian B. Shaw, Esq.; Harter Secrest & Emery LLP (57) ABSTRACT

A system for calculating cardiac output of a patient on an extracorporeal blood oxygenation circuit includes measuring first oxygenated blood flow rate by a pump in the extracorporeal circuit and a corresponding arterial oxygen saturation and recirculation in the extracorporeal circuit, then changing the pump flow rate, such as decreased, to produce a corresponding change in arterial oxygen saturation (wherein such change is outside of normal operating variances or drift), which change in the arterial oxygen saturation and recirculation are measured. From the first flow rate and the second flow rate along with the corresponding measured recirculation and the arterial oxygen saturation, the CO of the patient can be calculated, without reliance upon a measure of venous oxygen saturation. The system also includes an accommodation of oxygenation by the lungs of the patient during the extracorporeal blood oxygenation.

20 Claims, 3 Drawing Sheets

(52) U.S. Cl.
CPC ... *A61M 1/1698* (2013.01); *A61M 2205/3334* (2013.01); *A61M 2230/20* (2013.01)

(58) Field of Classification Search
CPC ...... A61M 2205/3334; A61M 2230/20; A61N 5/029; A61N 5/14525
See application file for complete search history.

(56) References Cited

U.S. PATENT DOCUMENTS

| | | | |
|---|---|---|---|
| 6,506,146 | B1 | 1/2003 | Mohl |
| 2004/0158133 | A1 | 8/2004 | Krivitski et al. |
| 2006/0052715 | A1* | 3/2006 | Krivitski ............... A61B 5/0275 600/508 |
| 2006/0211947 | A1* | 9/2006 | Krivitski ............... A61B 5/0275 600/526 |
| 2008/0033314 | A1 | 2/2008 | Krivitski |
| 2015/0316404 | A1* | 11/2015 | Krivitski ................ G01F 22/02 702/19 |
| 2016/0346448 | A1* | 12/2016 | Kaiser ................ A61N 1/36528 |
| 2020/0306437 | A1* | 10/2020 | Stern ................... A61M 1/3656 |

OTHER PUBLICATIONS

Korean Intellectual Property Office (ISA/KR), International Search Report and Written Opinion of the ISA from International Application No. PCT/US/2020/015016 dated May 27, 2020.

Joyce, Christopher John et al., "A Mathematical Modeo of CO2, O2 and N2 Exchange During Venovenous Extracorporeal Membrane Oxygenation", Intensive Care Medicine Experimental, 2018, vol. 6, article No. 25, pp. 1-13.

Broman, Mikael et al., "Recirculation During Veno-Venous Extra-Corporeal Membrane Oxygenation—A Simulation Study", The International Journal of Artificial Organs, 2015, vol. 38, No. 1, pp. 23-30.

Nunes, Liane Brescovici et al., "Severe Hypoxemia During Veno-Venous Extracorporeal Membrane Oxygenation: Exploring the Limits of Extracorporeal Respiratory Support", Clinic, 2014, vol. 69, No. 3, pp. 173-178.

* cited by examiner

METHOD AND APPARATUS FOR ASSESSING CARDIAC OUTPUT IN VENO-VENOUS EXTRACORPOREAL BLOOD OXYGENATION

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO A SEQUENCE LISTING

Not applicable.

STATEMENT REGARDING PRIOR DISCLOSURES BY THE INVENTOR OR A JOINT INVENTOR

Not applicable.

BACKGROUND OF THE INVENTION

The present disclosure relates to assessing cardiac output of a patient operably connected to a veno-venous (VV) extracorporeal circuit, and particularly to a veno-venous extracorporeal blood oxygenation circuit such as but not limited to a veno-venous extracorporeal membrane oxygenation (ECMO) circuit.

VV ECMO is a medical procedure employed in patients who are experiencing life-threatening respiratory failure, typically Acute Respiratory Distress Syndrome (ARDS). However, other indications include infection, such as viral, bacterial, fungus, PCP; primary lung disease, such as cystic fibrosis, hemorrhagic auto immune diseases; idiopathic fibrosis, sickle cell crisis, primary pulmonary hypertension; chest trauma, post pneumonectomy; post-transplant: acute, chronic (bronchiolitis obliterans); chronic respiratory failure bridging to transplant.

In these patients, blood that is passing the lungs is poorly oxygenated, and thus not enough oxygen is delivered to the tissue. This lack of oxygen delivery causes damage to the tissue and can ultimately the death of the patient. Extracorporeal blood oxygenation, such as VV ECMO, supplements or replaces blood oxygenation by the lungs of the patient.

In VV ECMO, large cannulas are inserted usually through femoral and/or jugular veins with the tip located in the superior and/or inferior vena cava or in the right atrium. These cannulae are then connected to an extracorporeal circuit which includes a pump and a membrane oxygenator. Blood is usually withdrawn from one (or two locations) and delivered close to the right atria, but there are multiple modifications. The patient blood is continuously circulated through the extracorporeal circuit, by being withdrawn from the patient, then circulated through an oxygenator, such as a membrane oxygenator, where the blood is then oxygenated. The blood is returned to the patient where the now oxygenated blood is pumped by right heart through lungs to left heart which delivers the oxygenated blood to the body tissue.

An important consequence of VV ECMO treatment is the occurrence of recirculation. Recirculation arises when a portion of the oxygenated blood that is being returned to the patient does not pass into the patient heart but is withdrawn into the extracorporeal circuit. This can occur due to poor positioning of the withdrawal and delivery cannulas, and/or if the patient has insufficient cardiac output to accept the full flow of oxygenated blood. Recirculation can be a problem during treatment, as the presence of recirculation means that some portion of the therapy being supplied to the patient is not actually assisting in their recovery.

The VV ECMO procedure is usually applied to patients that have a good working heart. During the course of VV ECMO, cardiac insufficiency (often right heart) may develop. This can be a life threatening situation. Sufficiency of circulation by the heart is typically assessed by measuring the cardiac output. Current standard methods to measure cardiac output (CO) such as pulmonary artery thermodilution and transpulmonary thermodilution are invasive as well as often inaccurate. In the VV ECMO setting, these methods may give misleading results, especially at high recirculation levels. As a result, a dramatic heart failure may be missed. An identified decrease in CO can be addressed by physicians either by medication therapy or by moving the patient to VA ECMO, where the extracorporeal circuit provides heart support in addition to lung support (though the VA ECMO is more invasive).

BRIEF SUMMARY OF THE INVENTION

Generally, the present disclosure provides a non-invasive method and apparatus to measure cardiac output, CO, in patients operably connected to a veno-venous extracorporeal circuit, and particularly a veno-venous extracorporeal blood oxygenation circuit such as but not limited to a veno-venous extracorporeal membrane oxygenation (ECMO) circuit.

In one configuration, a first flow rate from a pump in an extracorporeal circuit and an arterial oxygen saturation are measured and injection of an indicator, such as normal saline, is used to measure a recirculation in the extracorporeal circuit during the first flow rate, then the pump flow rate is changed, such as decreased (or increased), to produce a corresponding change in arterial oxygen saturation (such change being outside of variances or drift), which changes the arterial oxygen saturation and again an injection of saline is used to measure recirculation at the second flow rate from the pump and new oxygen saturation and recirculation measurements are recorded. The CO of the patient can be calculated from the first flow rate, the second flow rate, and the recirculation and the arterial oxygen saturation corresponding to each of the first flow rate and the second flow rate.

In one configuration a method is provided for calculating cardiac output of a patient undergoing veno-venous extracorporeal oxygenation, wherein the method includes withdrawing blood from a venous portion of a patient circulatory system to pass the withdrawn blood into a veno-venous extracorporeal circuit having an access (sometimes referred to as a venous) line, a return (sometimes referred to as an arterial) line and a blood oxygenator intermediate the access line and the return line, such that the withdrawn blood enters the extracorporeal circuit through the access line; passing the withdrawn blood through the access line and the blood oxygenator to form oxygenated blood; passing the oxygenated blood from the oxygenator and through the return line; introducing the oxygenated blood from the return line to the venous portion of the patient circulatory system; measuring a first blood flow rate through the extracorporeal circuit (such as in one of the access line, the blood oxygenator and the return line); measuring an arterial oxygen saturation of the patient; measuring a venous oxygen saturation of the patient; and calculating a cardiac output of the patient corresponding to the measured blood flow rate, the measured arterial oxygen saturation and the measured venous oxygen saturation. It is contemplated that measuring any of the parameters can include measuring a surrogate parameter.

In a further configuration, a method is provided for assessing cardiac output of a patient undergoing veno-venous extracorporeal blood oxygenation, wherein the method includes establishing a first blood flow rate from an extracorporeal blood oxygenation circuit into a venous portion of a patient circulation system; measuring the first blood flow rate; measuring a first arterial oxygen saturation of the patient corresponding to the first blood flow rate; measuring a first recirculation in the extracorporeal blood oxygenation circuit corresponding to the first blood flow rate; establishing a second blood flow rate from the extracorporeal blood oxygenation circuit into the venous portion of a patient circulation system; measuring the second blood flow rate; measuring a second arterial oxygen saturation of the patient corresponding the second blood flow rate; measuring a second recirculation in the extracorporeal blood oxygenation circuit corresponding the second blood flow rate; and calculating a cardiac output of the patient corresponding to the first blood flow rate, the second blood flow rate, the first arterial oxygen saturation, the second arterial oxygen saturation, the first recirculation and the second recirculation.

In another configuration, the method includes establishing a third blood flow rate in extracorporeal blood oxygenation circuit into the venous portion of a patient circulation system; measuring the third blood flow rate; measuring a third arterial oxygen saturation of the patient corresponding the third blood flow rate; measuring a third recirculation in the extracorporeal blood oxygenation circuit corresponding the third blood flow rate; and calculating a cardiac output of the patient corresponding to the first blood flow rate, the second blood flow rate, the third blood flow rate, the first arterial oxygen saturation, the second arterial oxygen saturation, the third arterial oxygen saturation, the first recirculation, the second recirculation and the third recirculation.

It is understood, that four or more blood flow rates can be established, and the measurements used to further calculate the cardiac output. Thus, in certain configurations there is at least one change in the flow rate from the extracorporeal circuit.

A further disclosed method includes is a method for assessing cardiac output of a patient undergoing veno-venous extracorporeal blood oxygenation, the method including the steps of measuring a blood flow rate of oxygenated blood delivered to a venous portion of a patient circulation system by an extracorporeal blood oxygenation circuit; measuring an arterial oxygen saturation of the patient; measuring a venous oxygen saturation of the patient; and calculating a cardiac output of the patient corresponding to the measured blood flow rate, the measured arterial oxygen saturation and the measured venous oxygen saturation. It is contemplated the method can include the further step of measuring a recirculation through the extracorporeal circuit and adjusting the calculation of cardiac output corresponding to the measured recirculation. It is further contemplated the method can include the further step of changing the blood flow rate of oxygenated blood delivered to the venous portion of the patient circulation system.

The present disclosure further contemplates an apparatus for quantifying a cardiac output of a patient operably connected to an extracorporeal blood oxygenation circuit, the extracorporeal blood oxygenation circuit having an access line withdrawing blood from a circulation system of the patient, a blood oxygenator, a pump and a return line returning oxygenated blood to a venous portion of the circulation system, wherein the apparatus includes: a controller configured to connect to one of the blood oxygenator and the pump, the controller configured to calculate a cardiac output of the patient based on a measured first flow rate of oxygenated blood from the extracorporeal circuit, a first recirculation during the first flow rate, a first arterial oxygen saturation of the patient during the first flow rate, a measured second flow rate of oxygenated blood from the extracorporeal circuit, a second recirculation during the second flow rate, and a second arterial oxygen saturation of the patient during the second flow rate.

It is further contemplated the apparatus can include a first sensor operably connected to the access line and a second sensor operably connected the return line. In one configuration, the access line can include an indicator injection port. It is understood a pulse oximeter can be used for measuring the arterial oxygen saturation.

The controller can also be configured to calculate the recirculation based on an introduced indicator.

A further apparatus is provided for calculating cardiac output of a patient undergoing veno-venous extracorporeal oxygenation through a veno-venous extracorporeal circuit, wherein the apparatus includes a controller, a pump connected to the veno-venous extracorporeal circuit for generating a blood flow through the veno-venous extracorporeal circuit, the pump operably connected to the controller and configured to generate a first blood flow rate through the veno-venous extracorporeal circuit and a different second blood flow rate through the veno-venous extracorporeal circuit; an oximeter connected to the controller for measuring a first arterial oxygen saturation corresponding to the first blood flow rate and a second arterial oxygen saturation corresponding to the second blood flow rate, wherein the controller is configured to calculate a cardiac output of the patient corresponding to the first measured arterial oxygen saturation, the second measured arterial oxygen saturation, the first blood flow rate and the second blood flow rate. In a further configuration, the controller is configured to calculate the cardiac output further corresponding to a first amount of recirculation during the first blood flow rate and a second amount of recirculation during the second blood flow rate. The controller can be further configured to adjust the calculated cardiac output by an amount corresponding to a first oxygen saturation of mixed venous blood after passing the lungs during the first blood flow rate and a second oxygen saturation of mixed venous blood after passing the lungs during the second blood flow rate. In one configuration, the controller is configured to adjust the calculated cardiac output by an amount corresponding to a difference between the first measured arterial oxygen saturation and the second measured arterial oxygen saturation. The controller can be further configured to adjust the calculated cardiac output by an amount proportional to a difference between the first measured arterial oxygen saturation and the second measured arterial oxygen saturation.

The following will describe embodiments of the present disclosure, but it should be appreciated that the present disclosure is not limited to the described embodiments and various modifications of the invention are possible without departing from the basic principles. The scope of the present disclosure is therefore to be determined solely by the appended claims.

DETAILED DESCRIPTION OF THE INVENTION

Figure 1:
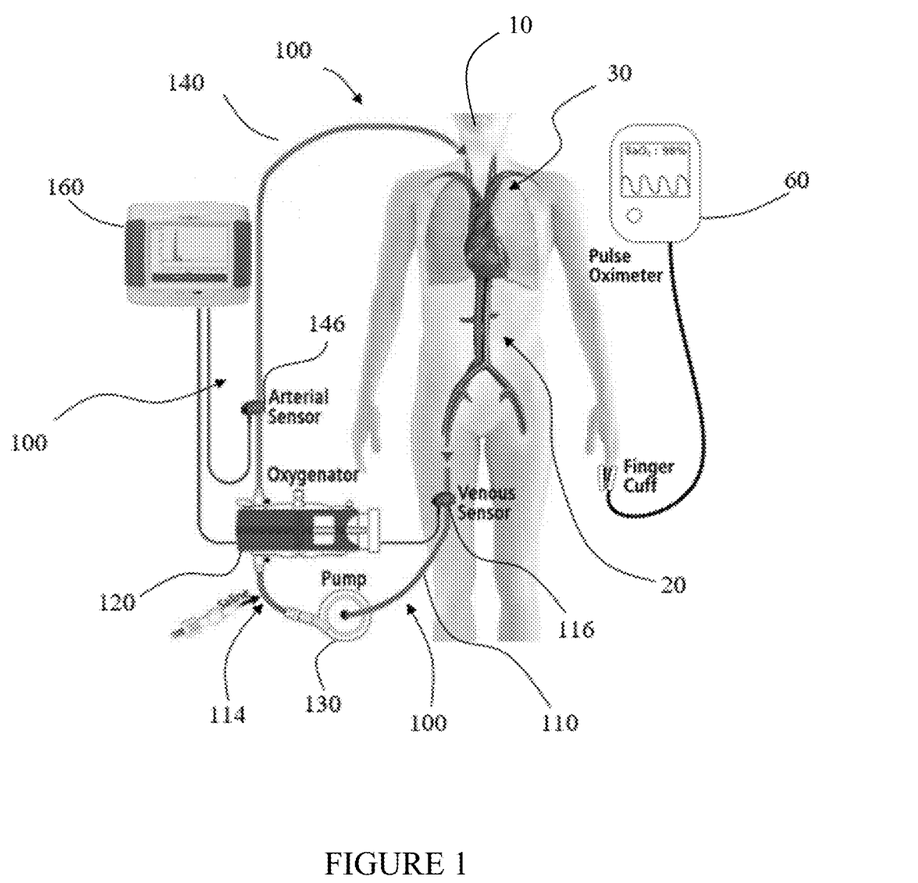
FIG. 1 is a representative veno-venous extracorporeal blood oxygenation circuit.

Referring to FIG. 1, an extracorporeal blood oxygenation circuit 100 is shown connected to a circulation system 20 of a patient 10.

The circulation system 20 is a human (or animal) circulatory system including blood, a vascular system, and a heart. For purposes of this description, the circulation system 20 is includes a cardiopulmonary system 30 and a systemic system connecting the cardiopulmonary system to the tissues of the body. Specifically, the systemic system passes the blood though the vascular system (arteries, veins, and capillaries) throughout the body.

The cardiopulmonary system 30 includes the right heart, the lungs and the left heart, as well as the vascular structure connecting the right heart to the lungs, the lungs to the left heart and some portion of the aorta and large veins located between the extracorporeal circuit and the right and left heart. That is, in theory the cardiopulmonary system 30 would include only the right heart, the lungs, the left heart and the vascular structure directly connecting the right heart to the lungs and the lungs to the left heart. However, in practice it is sometimes impracticable to operably connect the extracorporeal circuit 100 immediately adjacent the large vein at the right heart. Therefore, the cardiopulmonary system 30 often includes a limited length of the vein entering the right heart. For example, the extracorporeal circuit 100 can be connected to a femoral vein, thereby effectively extending the cardiopulmonary system 30 to such femoral vein.

For cardiopulmonary and vascular systems, the term "upstream" of a given position refers to a direction against the flow of blood, and the term "downstream" of a given position is the direction of blood flow away from the given position. The "arterial" side or portion is that part in which oxygenated blood flows from the heart to the capillaries. The "venous" side or portion is that part in which blood flows from the capillaries to the heart and lungs (to the cardiopulmonary system 30).

The basic components of the extracorporeal circuit 100 for a conventional extracorporeal oxygenation machine include an access (or venous) line 110, an oxygenator 120 and heat exchanger (not shown), a pump 130, a return (or arterial) 140, a sensor 116 in the venous line, a sensor 146 in the arterial line and a controller 160.

The extracorporeal circuit 100 is configured to form a veno-venous (VV) extracorporeal circuit 100. In the veno-venous extracorporeal circuit 100, the site of the withdrawal of blood from the circulation system 20 to the extracorporeal circuit 100 and the site of introduction of blood from the extracorporeal circuit to the circulation system both occur in the venous portion of the circulation system as seen in FIG. 2.

Figure 2:
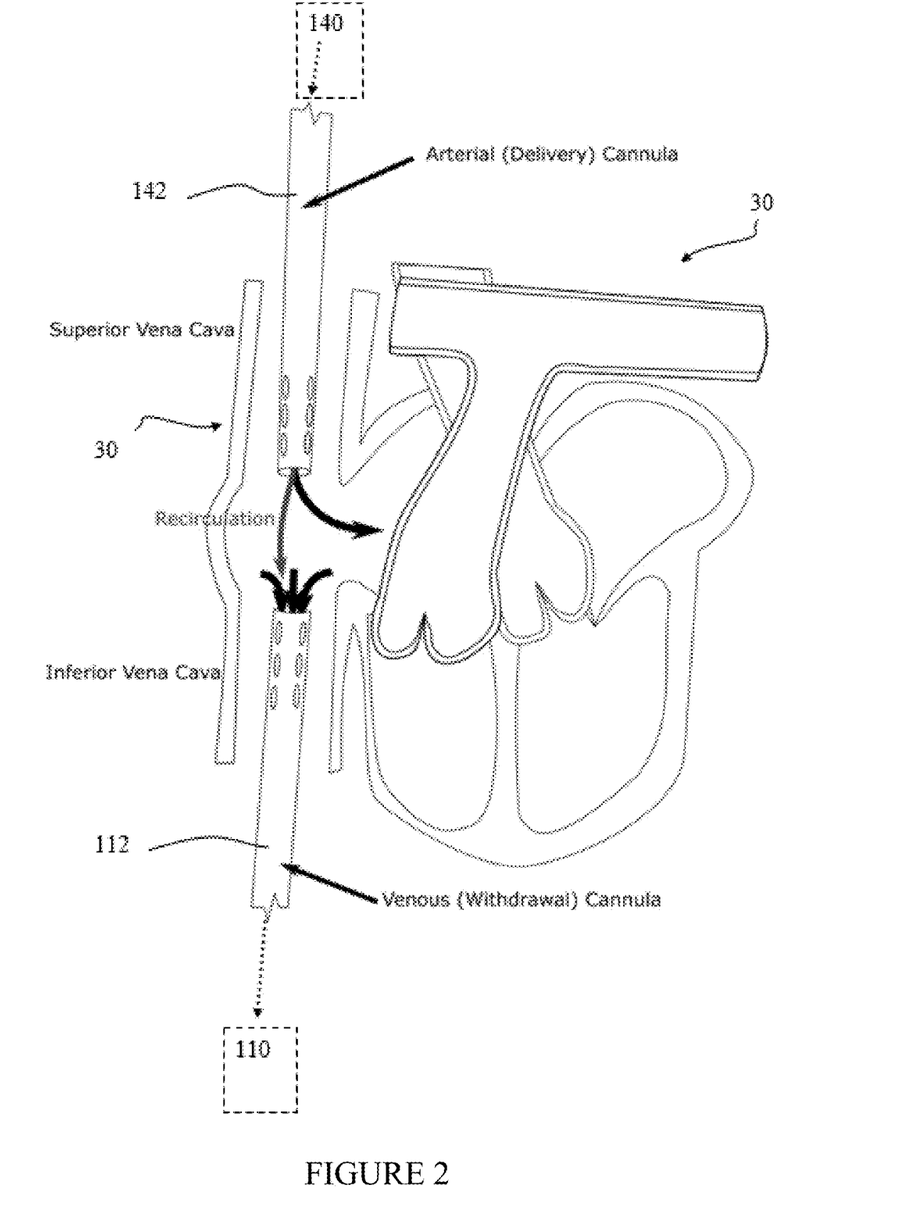
FIG. 2 is representation of the location of blood introduction and blood withdrawal in the veno-venous extracorporeal blood oxygenation circuit.

Referring to FIG. 2, in one configuration, the site of withdrawal of blood from the circulation system 20 to the extracorporeal circuit 100 is the inferior vena cava and the site of introduction of blood from the extracorporeal circuit to the circulation system is the superior vena cava.

Thus, the VV extracorporeal circuit 100 withdraws blood from the venous portion of the circulation system 20 (or cardiopulmonary system 30), and returns the blood to the venous portion of the circulation system. The withdrawn blood can be treated while it is withdrawn, such as through gas exchange or oxygenation (ECMO) before being returned to the venous portion of the circulation system 20. The blood treatment can be any of a variety of treatments including, but not limited to, oxygenation (and carbon dioxide withdrawal).

Generally, the access line 110 withdraws or drains blood from the patient and into the extracorporeal circuit 100. The access line 110 extends from the venous portion of the circulation system 20, and preferably from a venous portion of the cardiopulmonary system 30. Referring to FIG. 2, the access line 110 typically includes an access cannula 112 providing the fluid connection to the circulation system 20.

The access line 110 can also include or provide an introduction site such as an indicator introduction port 114 as the site for introducing an indicator into the extra corporeal circuit 100. In one configuration, the indicator introduction port 114 for introducing the dilution indicator is upstream to an inlet of the oxygenator 120. In selected configurations, the introduction site 114 can be integrated into the oxygenator 120.

In the access line 110, the sensor 116, can be a dilution sensor for sensing passage of the indicator through the extracorporeal circuit 100. However, it is understood, the dilution sensor 116 (as well as sensor 146) can be any of a variety of sensors, and can cooperate with the particular indicator. The sensor 116 (as well as sensor 146) can measure different blood properties: such as but not limited to temperature, Doppler frequency, electrical impedance, optical properties, density, ultrasound velocity, concentration of glucose, oxygen saturation and other blood substances (any physical, electrical or chemical blood properties). It is also understood the sensor 116 can also measure the blood flow rate. Alternatively, there can a separate flow sensor (not shown) in addition to sensor 116 be to measure the blood flow rate. Thus, in one configuration the present system includes a single blood property sensor and a single flow rate sensor. It is further contemplated that a single combined sensor for measuring flow rate and a blood parameter (property) can be used. As set forth herein, in some pumps 130, a rotational speed, RPM (rotations per minute) of the pump can be measured for providing a measurement of blood flow rate.

The return line 140 connects the extracorporeal circuit 100 to a venous portion of the circulation system 20 and in one configuration to a venous portion of the cardiopulmonary system 30. The return line 140 usually connects to the superior vena cava but may connected to right atria (tip position) or inferior vena cava. The return line 140 typically includes a return (arterial) cannula 142 providing the fluid connection to the circulation system 20.

The return line 140 can also include a sensor such as the sensor 146. The sensor 146 can be any of a variety of sensors, as set forth in the description of the sensor 116, and is typically selected to cooperate with the anticipated indicator.

However, it is understood the sensors 116, 146 can be located outside of the extracorporeal circuit. That is, the sensors 116, 146 can be remotely located and measure in the extracorporeal circuit 100, the changes produced in the blood from the indicator introduction or values related to the indicator introduction which can be transmitted or transferred by means of diffusion, electro-magnetic or thermal fields or by other means to the location of the sensor. Although two sensors are shown, it is understood only a single sensor is necessary in order to measure a recirculation. While use of two sensors can improve accuracy, it is not necessary that two sensors be employed to calculate recirculation.

The oxygenator 120 can be broadly classified into bubble type oxygenators and membrane type oxygenators. The membrane type oxygenators fall under the laminate type, the coil type, and the hollow fiber type. Membrane type oxygenators offer advantages over the bubble type oxygenators as the membrane type oxygenators typically cause less blood damage, such as hemolysis, protein denaturation, and blood coagulation as compared with the bubble type oxygenators. Although the preferred configuration is set forth in terms of a membrane type oxygenator, it is understood any type of oxygenator can be employed.

The pump 130 can be any of a variety of pumps types, including but not limited to a peristaltic or roller (or impeller or centrifugal) pump. The pump 130 induces a blood flow rate through the extracorporeal circuit 100. Depending on the specific configuration, the pump 130 can be directly controlled at the pump or can be controlled through the controller 160 to establish a given blood flow rate in the extracorporeal circuit 100. The pump 130 can be at any of a variety of locations in the extracorporeal circuit 100, and is not limited to the position shown in the Figures. In one configuration, the pump 130 is a commercially available pump and can be set or adjusted to provide any of a variety of flow rates, wherein the flow rate can be read by a user and/or transmitted to and read by the controller 160.

The controller 160 is typically connectable to the oxygenator 120, the pump 130 and the sensor(s) 116, 146. The controller 160 can be a stand-alone device such as a personal computer, a dedicated device or embedded in one of the components, such as the pump 130 or the oxygenator 120. Although the controller 160 is shown as connected to the sensors 116 and 146, the pump 130 and the oxygenator 120, it is understood the controller can be connected to only the sensors, the sensors or the pump, or any combination of the sensors, the pump and the oxygenator. In one configuration, at least one of the pump 130 and the controller 160 provides for control of the pump and the flow rate of the blood through the pump, respectively. It is also understood, the controller 160 also can be connected to the oximeter to automatically collect data or oximetry data can be put manually into controller. Alternatively, a pulse oximeter 60 and the controller 160 can be integrated as a single unit.

The controller 160 is programmed with the equations as set forth herein and can perform the associated calculations based on inputs from the user and/or connected components.

The normal or forward blood flow through the extracorporeal circuit 100 includes withdrawing blood through the access line 110 from the venous side of the circulation system 20 (and particularly the cardiopulmonary circuit 30), passing the withdrawn blood through the extracorporeal circuit (to treat such as oxygenate), and introducing the withdrawn (or treated or oxygenated) blood through the return line 140 into the venous side of the circulation system. The pump 130 thereby induces a blood flow at a known (measured) blood flow rate through the extracorporeal circuit 100 from the access line 110 to the return line 140.

For purposes of the present description, the following terminology is used. Cardiac output CO is the amount of blood pumped out by the left ventricle in a given period of time (typically a 1 minute interval). The heart capacity (flow) is typically measured by cardiac output CO. The term blood flow rate means a rate of blood passage, volume per unit time. The blood flow rate is a volumetric flow rate ("flow rate"). The volumetric flow rate is a measure of a volume of liquid passing a cross-sectional area of a conduit per unit time, and may be expressed in units such as milliliters per min (ml/min) or liters per minute (l/min).

The present disclosure provides a simple noninvasive technology to measure cardiac output, CO in VV extracorporeal blood oxygenation, such as a VV ECMO setting. To apply the present technique to measure CO during VV extracorporeal blood oxygenation, including ECMO, the following terms are employed:

$SvO_2$ is the mixed venous oxygen saturation of blood that did not pass through the oxygenator 120

$SaO_2$—arterial oxygen saturation, (which as set forth below can be measured by blood sample or by pulse oximetry)

$Q_b$ is the extracorporeal circuit flow rate, (which as set forth below can be measured by a flow rate of the pump 130 in the extracorporeal circuit)

R % is the percentage recirculation (%)

CO is the cardiac output

Balance Equation

In the first instance, a mass balance equation is applied to the extracorporeal circuit. For this analysis, the following assumptions are made:

1. Oxygenation in the lungs is small (negligible).
2. Oxygen Saturation of the blood after oxygenator is at or near 100%. (The formula below can be adjusted for a different value of oxygen saturation from the oxygenator 120).
3. No recirculation.

With the appropriate accounting for oxygen, an initial equation becomes:

$$Q_b * 100 + (CO - Q_b) * SvO_2 = CO * SaO_2 \quad \text{Eq. 1}$$

Solving for CO:

$$Q_b^* 100 + CO^* SvO_2 - Q_b^* SvO_2 = CO^* SaO_2 \quad \text{Eq. 2}$$

$$CO \times (SaO_2 - SvO_2) = Q_b \times (100 - SvO_2) \quad \text{Eq. 3}$$

$$CO = Q_b \times \frac{(100 - SvO_2)}{(SaO_2 - SvO_2)} \quad \text{Eq. 4}$$

Currently, during VV ECMO treatment, $Q_b$ and $SaO_2$ are routinely measured, while $SvO_2$ is difficult to measure. That is, the value of venous oxygen saturation measured pre-oxygenator in the extracorporeal (ECMO) circuit 100 may be different from mixed venous oxygen saturation in the cardiopulmonary system 30—as well as being subject to influence from the presence of any recirculation.

Therefore, Equation 4 can be used with the measured and reliable values of $Q_b$ and $SaO_2$ in conjunction with a measured $SvO_2$, such as measured in the access line 110, recognizing the measured surrogate value of $SvO_2$ value may introduce an unacceptable error in certain instances, especially in the case of the presence of recirculation.

Thus, depending on the confidence in the $SvO_2$ value, there are 2 unknowns in Equation 4 for low maintenance in the value of measured $SvO_2$, or the equation can still be used for CO assessment with an acceptable measurement of $SvO_2$, but is less accurate.

Balance Equation with Recirculation

A further configuration of the present system can incorporate an accounting of recirculation. Referring to FIG. 2, in veno-venous extracorporeal blood oxygenation, such as VV ECMO, recirculation is the withdrawal of reinfused oxygenated blood through the access (drainage) cannula 112 without the reinfused oxygenated blood passing through the circulation system 20. Because recirculated blood does not contribute to oxygen delivery in the circulation system 20, the presence of recirculation decreases the efficiency of the extra corporeal blood oxygenation (ECMO) procedure.

In case of recirculation, the actual effective flow, $Q_{eff}$, that carries 100% oxygenated blood into heart will be:

$$Q_{eff} = Q_b \times \left(1 - \frac{R\%}{100}\right) \qquad \text{Eq. 5}$$

Replacing $Q_b$ with $Q_{eff}$ in Equation 4, yields:

$$CO = Q_{eff} \times \frac{(100 - SvO_2)}{(SaO_2 - SvO_2)} \qquad \text{Eq. 4A}$$

Substituting $Q_b$ for $Q_{eff}$ provides:

$$CO = Q_b \times \frac{\left(1 - \frac{R\%}{100}\right) \times (100 - SvO_2)}{(SaO_2 - SvO_2)} \qquad \text{Eq. 4B}$$

The value of venous oxygen saturation measured pre-oxygenator in the extracorporeal (ECMO) circuit 100 will differ even more from the mixed venous oxygen saturation in the presence of recirculation. Thus, to use measured $SvO_2$ at the inlet of the blood oxygenator 120 (ECMO), one needs to use the following equation:

Taking the oxygen saturation balance at the inflow of oxygenator:

$$Q_b * SvO_{2 \text{ at ECMO inlet}} = Q_b * R\% + Q_b[1 - R\%/100] * SvO_{2 \text{ in the venous vessel}} \qquad \text{Eq. 8}$$

Where Equation 8 can be rewritten as:

$$SvO_{2 \text{ in the venous vessel}} = [SvO_{2 \text{ at ECMO inlet}} - 100 * R\%/100]/[1 - R\%/100] \qquad \text{Eq. 9}$$

Which simplifies to:

$$SvO_{2 \text{ in the venous vessel}} = [SvO_{2 \text{ at ECMO inlet}} - R\%]/[1 - R\%/100] \qquad \text{Eq. 9A}$$

The value of $SvO_{2 \text{ in the venous vessel}}$ may be used in Eq. 4B instead of $SvO_2$, but this substitution will result in an error in the calculated CO from substitution of the mixed venous oxygen saturation by the oxygen saturation from the vessels where the oxygen saturation was sampled.

Two Balance Equations with Recirculation

To increase the accuracy of the CO measurement with the purpose of the elimination of the potentially unreliable or unknown value of $SvO_2$, the value of $Q_b$ (such as via flow rate of the pump 130 in the extracorporeal circuit 100) can be changed, such as by an increase or decrease to deliver a different flow rate of 100% oxygenated blood through the return line 140 and into the heart.

For purposes of description, assume the flow of oxygenated blood from the oxygenator is decreased, such as by decreasing pump flow (where $Q_{b(2)} < Q_{b(1)}$). Thus, less 100% oxygenated blood is delivered from the extracorporeal circuit 100 and measured on the arterial side of the patient, $SaO_2(2) < SaO_2(1)$. From this difference, a change in $SaO_2$, $\Delta SaO_2$, can be written as:

$$\Delta SaO_2 = SaO_{2(1)} - SaO_{2(2)} \qquad \text{Eq. 10}$$

where index "(1)" and "(2)" correspond to a first flow rate delivered by the extracorporeal circuit 100, such as a first pump setting, $Q_{b(1)}$ and a second flow rate delivered by the extracorporeal circuit, such as a second pump setting pump setting $Q_{b(2)}$, respectively.

For this application of two balance equations analogous to Eq. 4B, it is assumed the value of CO between the two flows through the extracorporeal circuit 100 does not change or that any actual change is insubstantial or negligible. Thus, the two equations for the two different flow rates of oxygenated blood from the extracorporeal circuit 100 are:

$$CO = Q_{b(1)} \times \frac{\left(1 - \frac{R\%_{(1)}}{100}\right) \times (100 - SvO_{2(1)})}{(SaO_{2(1)} - SvO_{2(1)})} \qquad \text{Eq. 11}$$

$$CO = Q_{b(2)} \times \frac{\left(1 - \frac{R\%_{(2)}}{100}\right) \times (100 - SvO_{2(2)})}{(SaO_{2(2)} - SvO_{2(2)})} \qquad \text{Eq. 12}$$

It can be seen that in case of no recirculation, these equations will be analogous to Eq. 4.

During the decrease in $SaO_2$ from $SaO_{2(1)}$ to $SaO_{2(2)}$, a decrease of $SvO_2$ is also expected. However, the magnitude of this decrease in $SvO_2$ is unknown. If the magnitude of the decrease in $SaO_2$ is small, then the assumption is made that $SvO_{2(1)} \approx SvO_{2(2)}$, then the system of equations (Eq. 11 and Eq. 12) with 2 unknowns (CO and $SvO_2$) can be solved for CO, which in turn can then be calculated from the known or measured $Q_{b(1)}$, $Q_{b(2)}$, % $R_{(1)}$ and % $R_{(2)}$, $SaO_{2(1)}$ and $SaO_{2(2)}$, without relying upon a value of $SvO_2$.

For example, if the magnitude of the decrease in $SaO_2$ is small, then the assumption is made that $SvO_{2(1)} \approx SvO_{2(2)}$, and the system of equations (Eq. 11 and Eq. 12) provide:

$$CO = Q_{b(2)} \left( \frac{\left(1 - \frac{R\%_{(2)}}{100}\right) \times (100 - A)}{(SaO_{2(2)} - A)} \right)$$

$$\text{Where } A = \frac{\left(100 \times Q_{b(1)} \times \left(1 - \frac{R\%_{(1)}}{100}\right) - CO \times SaO_{2(1)}\right)}{\left(\left(Q_{b(1)} \times \left(1 - \frac{R\%_{(1)}}{100}\right)\right) - CO\right)}$$

Further, if recirculation were not measured and the magnitude of the decrease in $SaO_2$ is small, then the assumption is made that $SvO_{2(1)} \approx SvO_{2(2)}$, then the system of equations (Eq. 11 and Eq. 12) provide:

$$CO = Q_{b(2)}\left(\frac{(100-A)}{(SaO_{2(2)}-A)}\right)$$

$$\text{where } A = \frac{(100 \times Q_{b(1)} - CO \times SaO_{2(1)})}{(Q_{b(1)} - CO)}$$

Conversely, if the decrease of $SvO_{2(1)}$ is as large as the decrease of arterial oxygen saturation, $\Delta SaO_2$, (Eq.10) then $\Delta SvO_2 = \Delta SaO_2$, or:

$$\Delta SaO_2 = SaO_{2(1)} - SaO_{2(2)} = \Delta SvO_2 = SvO_{2(1)} - SvO_{2(2)}$$

From this equation, $SvO_{2(2)}$ can be calculated as:

$$SvO_{2(2)} = SvO_{2(1)} - \Delta SaO_2 \quad \text{Eq. 13}$$

Substituting the above in to Eq.11 and 12 gives:

$$CO = Q_{b1} \times \frac{\left(1 - \frac{R\%_{(1)}}{100}\right) \times (100 - SvO_{2(1)})}{(SaO_{2(1)} - SvO_{2(1)})} \quad \text{Eq. 11A}$$

$$CO = Q_{b(2)} \times \frac{\left(1 - \frac{R\%_{(2)}}{100}\right) \times (100 - SvO_{2(1)} - SaO_{2(1)} + SaO_{2(2)})}{(SaO_{2(1)} - SvO_{2(1)})} \quad \text{Eq. 12A}$$

Again, a system of two equations with 2 unknowns (CO and $SvO_2$) is provided, wherein the equations can be solved to determine CO, without requiring a value or measurement of $SvO_2$.

Theoretically, it is believed the actual CO will be between value calculated from Equations 11-12 and the value calculated from Equations 11A-12A. Practically, it is observed that after a decrease of arterial oxygen saturation, the venous oxygen saturation also decreases. Thus, the CO value provided by Equations 11A-12A should be more accurate.

In case of the lungs partly working (thereby partly oxygenating the blood) the actual mass balance equations need to include an after lung oxygen saturation instead of venous oxygen saturation. The benefit of the current two flow rate approach is that it is independent of (eliminates) the need for assumptions of the venous oxygen saturations in Eq.4 (A, B) instead of a mix venous oxygen saturation. In addition, there may be intermediate conditions (assumptions) applied to Equations 11-12 and Equations 11A-12A, like the assumption that $SvO_{2(2)}$ does not decrease the entire amount of decrease in $SaO_2$ as per $\Delta SaO_2$, but on a portion such as ⅓ or ⅕ etc., then all the solutions for the CO value will be between Equations 11-12 and Equations 11A-12A.

In application, the CO of the patient on extracorporeal blood oxygenation, such as VV-ECMO can be obtained in the following configurations.

In one configuration, the patient, and particularly the circulation system 20, is operably connected to the extracorporeal circuit 100, wherein the access line 110, which can include the cannula (an access cannula) 112 as known in the art, withdraws blood from the patient, and particularly the venous portion of the circulation system 20 and in one configuration from the inferior vena cava.

The withdrawn blood is passed through the access line 110 through the pump 130 and to the oxygenator 120. The blood is oxygenated in the oxygenator 120 and then pumped through the return line 140 for introduction of the oxygenated blood to the patient, and particularly the circulation system 20 and more particularly the venous portion of the circulation system 20, and more particularly the venous side of the cardiopulmonary system 30, such as the superior vena cava.

To calculate the CO, amount (flow rate) of oxygenated blood introduced into the circulation system 20 is measured, such as by reading the volumetric pump flow setting of the pump 130. However, it is understood alternative mechanisms can be used to measure the flow of oxygenated blood, such as by not limited to, flow meters in the extracorporeal circuit 100, dilution measurements, ultrasonic measurements as known in the art.

The arterial oxygen saturation, $SaO_2$, is measured such as by pulse oximetry or arterial blood gas analysis. As seen in FIG. 1, a pulse oximeter 60 is connected to the patient to measure arterial oxygen saturation, $SaO_2$.

The venous oxygen saturation, $SvO_2$, is measured at the inlet of the oxygenator in the extracorporeal circuit 100. It is understood this measurement is not of mixed venous oxygen saturation, but is rather measurement of a surrogate. However, in view of the invasion nature and potential complications inherent in drawing blood from the pulmonary artery, the measurement of oxygen saturation from the blood drawn from the inferior vena cava is used.

It is noted that the method for calculating CO is not limited to the manner of measurement of the parameter upon which the CO is calculated.

Then assuming no, or negligible recirculation, the CO is calculated by:

$$CO = Q_b \times \frac{(100 - SvO_2)}{(SaO_2 - SvO_2)} \quad \text{Eq. 4}$$

The recirculation can also be measured by any of the following mechanisms known in the art:

| Method of estimating % recirculation | Description |
| --- | --- |
| CVL (Central Venous Line) | Formula: $(S_{pre}O_2 - SvO_2)/(S_{post}O_2 - SvO_2) \times 100$<br>$SvO_2$ estimated by measuring venous oxygen saturation of blood from SVC (superior vena cava) or IVC (inferior vena cava) via central venous catheter |
| $SvO_2$ | Formula: $(S_{pre}O_2 - SvO_2)/(S_{post}O_2 - SvO_2) \times 100$<br>$SvO_2 = S_{pre}O_2$ when sweep gas turned off and ventilator used to achieve an equivalent $SaO_2$ |
| Ultrasound dilution[#12] | Saline injected into reinfusion limb; ultrasound sensor detects differences in dilution between drainage and reinfusion limb |
| Thermodilution | Cold saline injected into reinfusion limb; thermistor-tipped catheter detects changes in temperature in drainage limb |
| Trending $S_{pre}O_2$ | Observation of changes in SpreO2 and SaO2 over time; increasing $SpreO_2$ and decreasing $SaO_2$ suggest clinically relevant recirculation | where CVL = central venous line
ECMO = extracorporeal membrane oxygenation
IVC = inferior vena cava
SVC = superior vena cava
$SaO_2$ = oxygen saturation of arterial blood
$S_{pre}O_2$ = oxygen saturation of blood entering the membrane oxygenator
$S_{post}O_2$ = oxygen saturation of blood leaving the membrane oxygenator
$SvO_2$ = oxygen saturation of venous blood returning to the vena cava Thus, as set forth above to accommodate the presence of recirculation, Eq. 4B is used.

$$CO = Q_b \times \frac{\left(1 - \frac{\%R}{100}\right)(100 - SvO_2)}{(SaO_2 - SvO_2)} \qquad \text{Eq. 4B}$$

In an alternative configuration employing select equations from above, the patient is operably connected to the extracorporeal circuit 100 as set forth above. It is further understood that although the present method is set forth with specific manner of obtaining measurements, any available manner of obtaining the identified data can be employed.

In this alternative configuration, the amount of oxygenated blood introduced into the patient circulation system 20 is identified by the setting of the pump 130. Recirculation, R, and arterial oxygen saturation, $SaO_2$, are measured, such as set forth above.

The flow rate of oxygenated blood from the extracorporeal circuit 100 and introduced to the circulation system 20 is then changed by an amount sufficient to generate a corresponding change to the measured $SaO_2$. Further, in one configuration the amount of change in the flow rate of oxygenated blood from the extracorporeal circuit 100 is sufficient to impart a change in the measured $SaO_2$ that is greater than operating error, drift or variance. In some configurations, the change in flow rate of oxygenated blood from the extracorporeal circuit 100 is at least 10% of the original flow rate, and in further configurations at least 20% of the original flow rate, an in other configurations at least 30% of the original flow rate. It is understood the change in flow rate of oxygenated blood from the extracorporeal circuit 100 can be as depending on the particular set of circumstances in order to generate the corresponding changes in the blood parameter such as arterial oxygen saturation, without deviating from the present system.

The change in the flow of oxygenated blood from the extracorporeal circuit 100 to the circulation system 20 can be readily imparted by changing the operation of the pump 130. Thus, a second flow rate of oxygenated blood is introduced into the circulation system 20.

After changing the oxygenated blood flow rate of the extracorporeal circuit 100, approximately 1 minute to 2 minutes can elapse before measuring the arterial oxygen saturation and the recirculation corresponding to the second flow rate.

Recirculation, R, and arterial oxygen saturation, $SaO_2$, are measured, such as set forth above, during the second flow rate of oxygenated blood passing into the circulation system 20.

Of note, there is no need for a measurement of $SvO_2$ or a surrogate parameter in this configuration. The CO can then be calculated through Eq. 11 and 12 or Eq. 11A and 12A from the measured first and second flow rate of oxygenated blood introduced into the circulation system 20, and the corresponding recirculation and arterial oxygen saturation, $SaO_2$ for each flow rate.

In a further configuration, the dilution sensors on the access line 110 and the return line 140 are used in conjunction with the introduction of an indicator, such as saline, at the indicator introduction port 114. Recirculation is then measured from the introduced indicator and measurement of the indicator at the sensors as known in the art.

The arterial oxygen saturation, $SaO_2$, is also measured as set forth above.

A different second flow rate of oxygenated blood is then imposed in the extracorporeal circuit 100 sufficient to impart a change in at least the arterial oxygen saturation, $SaO_2$ wherein the measured change is outside operating variances or drift, such as set forth above.

The pump flow rate of the second flow rate is recorded and the recirculation again measured, such as by the dilution technique. Arterial oxygen saturation, $SaO_2$ is also measured during or corresponding to the second flow rate.

Again, CO can be determined from Eq. 11 and 12 or Eq. 11A and 12A from the measured first and second flow rate of oxygenated blood introduced into the circulation system 20, and the corresponding recirculation and arterial oxygen saturation, $SaO_2$ for each flow rate.

As set forth in the above analysis, any contribution of oxygenation from the lungs was taken as small (negligible). However, accuracy of the assessment or calculation of CO can be further improved if oxygenation contribution from the lungs are taken into account or estimated.

Single mass balance equation incorporating lung contribution to blood oxygen saturation in VV ECMO patient It can be assumed that there is a combination of two flows passing through cardiopulmonary system 30. The first flow is the well oxygenated blood from the extracorporeal circuit 100 and the second flow is the less oxygenated venous (mixed venous) blood from the organs. The mixture of these two flows defines the saturation of oxygen in the cardiac output CO. For the pulmonary artery, the following two component equation provides a mass balance for oxygen saturation carried by hemoglobin in VV ECMO:

$$CO*S_{PA}O_2 = Q_{eff}*Sa_{OX}O_2 + (CO - Q_{eff})*S_VO_2 \qquad \text{Eq. 14}$$

Where $Q_{eff}$ is part of the flow from the extracorporeal circuit (ECMO) flow that enters the heart accounting for recirculation;

$Sa_{ox}O_2$ is the oxygen saturation of blood after the oxygenator 120 (approximately 100%);

CO is the cardiac output;

$SvO_2$ is the mixed venous oxygen saturation of blood entering the right atrium from the veins (not passed through oxygenator 120); and $S_{PA}O_2$ is the oxygen saturation of blood in the pulmonary artery.

As set forth above $Q_{eff}$ is defined as $$Q_{eff} = Q_b \times \left(1 - \frac{R\%}{100}\right) \qquad \text{Eq. 15}$$

where $Q_b$ is the extracorporeal circuit flow rate; and
R % is the percentage recirculation.

Assuming the lungs are partially functioning, then the balance equation becomes:

$$CO*SaO_2 = CO*S_{PA}O_2 + Res_L = Q_{eff}*Sa_{OX}O_2 + (CO - Q_{eff})*S_VO_2 + Res_L \qquad \text{Eq. 16}$$

where $Res_L$ is the oxygen added by the lungs; and
$SaO_2$ is the arterial oxygen saturation.

The venous and lung function can then be associated as follows:

$$CO*SaO_2 = Q_{eff}*Sa_{ox}O_2 + (CO - Q_{eff})\left(S_VO_2 + \frac{Res_L}{CO - Q_{eff}}\right) \qquad \text{Eq. 17}$$

Then $$S_LO_2 = S_vO_2 + \frac{Res_L}{CO - Q_{eff}} \quad \text{Eq. 18}$$

where $S_LO_2$ is the oxygen saturation of mixed venous blood after passing the lungs.

Finally, the mass balance equation for oxygen saturation across the whole cardiopulmonary system 30 will be:

$$CO*SaO_2 = Q_{eff}*Sa_{ox}O_2 + (CO - Q_{eff})*S_LO_2 \quad \text{Eq. 19}$$

As shown in Eq. 19, there is a sense where one can think of the lungs only changing the oxygen saturation of the venous portion of the blood as the blood after oxygenator is already 100% oxygen saturated. While in fact, as seen in FIG. 3, the oxygenated blood from the lungs acting on the mixture is a useful concept for the purpose of analyzing Eq. 19.

Figure 3:
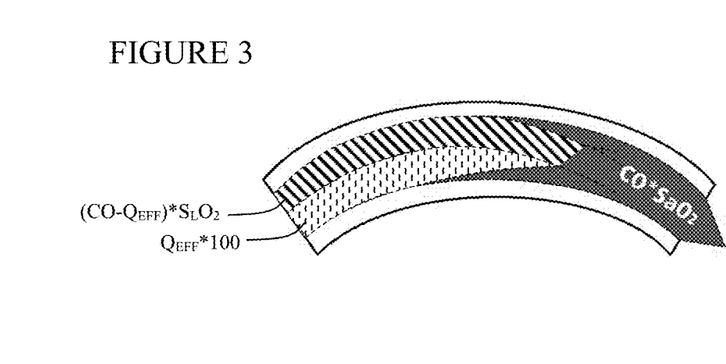
FIG. 3 is a schematic representation of the components of oxygenation of the blood delivered to the arterial side of a patient circulation system.

In Eq. 19, and referring to FIG. 3, the values of $SaO_2$, and $Q_{eff}$ can be measured if recirculation is measured, but the values of CO and $S_LO_2$ are unknown. Thus, there is one equation with two unknowns.

In an effort to reduce the number of unknowns relative to the number of equations, a second equation is generated as set forth below.

Two Mass Balance Equation Incorporating Lung Contribution to Blood Oxygen Saturation in VV ECMO Patient A resolution of the single equation and two unknowns is to obtain a second equation, thereby presenting two equations with two unknowns, which can be mathematically solved. To produce the second equation, the extracorporeal circuit flow rate, ECMO flow, is changed to present a measurable change in arterial oxygen saturation $SaO_2$, which change is greater than normal operating variances or drift.

Figure 4:
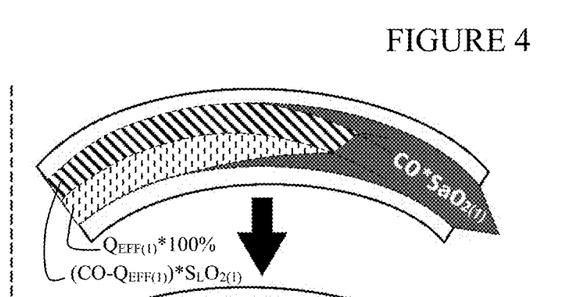
FIG. 4 is a schematic representation of the components of oxygenation of the blood delivered to the arterial side of a patient circulation system at a first blood flow rate from the extracorporeal circuit.
Figure 5:
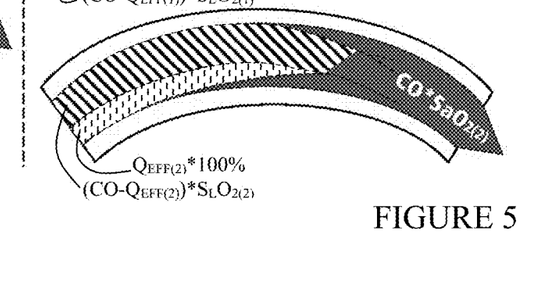
FIG. 5 is a schematic representation of the components of oxygenation of the blood delivered to the arterial side of a patient circulation system at a second, smaller, blood flow rate from the extracorporeal circuit.

While the change in extracorporeal circuit flow rate could be an increase or decrease, for purposes of description, a decrease is employed so as to generate a corresponding decrease in the arterial oxygen saturation $\Delta SaO_2$. This decrease in the arterial oxygen saturation is due to less of flow of the 100% saturated blood component coming from the oxygenator 120 and more flow of the less oxygenated mixed venous blood component coming from organs, as seen in FIGS. 4 and 5. This change in extracorporeal flow rate creates a second mass balance equation.

Thus, from Eq. 19, $$CO*SaO_{2(1)} = Q_{eff(1)}*Sa_{ox}O_{2(1)} + (CO - Q_{eff(1)})*S_LO_{2(1)} \quad \text{Eq. 20A}$$

$$CO*SaO_{2(2)} = Q_{eff(2)}*Sa_{ox}O_{2(2)} + (CO - Q_{eff(2)})*S_LO_{2(2)} \quad \text{Eq. 20B}$$

In the two equation system, 20A and 20B, index "1" and "2" denote the respective value as related to the first flow rate from the extracorporeal circuit 100 and the second flow rate from the extracorporeal circuit, respectively. As set forth above, for purposes of description the change in flow rate in the extracorporeal circuit is taken as $Q_{eff(1)} > Q_{eff(2)}$. That is, the pump flow can be decreased, thereby decreasing the extracorporeal circuit flow rate.

Equations 20A and 20B assume that CO does not change during the extracorporeal circuit 100 (pump flow) decrease or the change in CO is negligible. However, there are now two equations and three unknowns: CO, $S_LO_{2(1)}$ and $S_LO_{2(2)}$. Again, as there are more unknowns than equations, the system of equations cannot be solved directly.

The next step of the present modeling is to approximate a solution of current system of equations by considering the relationship between $S_LO_{2(1)}$ and $S_LO_{2(2)}$.

In response to the arterial oxygen saturation $SaO_2$ decrease, it is expected that mixed venous oxygen saturation $SvO_2$ also may change, which can be expressed as:

$$S_vO_{2(2)} = S_vO_{2(1)} - \Delta S_VO_2 \quad \text{Eq. 21}$$

Then assuming that during the arterial oxygen saturation decrease, the residual lung function does not change or only changes negligibly, then the following equation can be produced from Eq. 18 and Eq. 21:

$$S_LO_{2(2)} = S_LO_{2(1)} - \Delta SvO_2 \quad \text{Eq. 22}$$

For simplicity, a coefficient K is introduced as the then ratio of changes in the mixed venous oxygen saturation to the changes in the arterial oxygen saturation:

$$K = \frac{\Delta S_vO_2}{\Delta S_aO_2} \quad \text{Eq. 23}$$

Then, Eq. 22 can be rewritten based on Eq. 23:

$$S_LO_{2(2)} = S_LO_{2(1)} - K*\Delta SaO_2 \quad \text{Eq. 24}$$

Alternatively, Eq. 24 can be written as:

$$K*\Delta SaO_2 = S_LO_{2(1)} - S_LO_{2(2)} \quad \text{Eq. 24B}$$

Equation 24 suggests that even if an actual value of post venous lung oxygen saturation is not known, but the changes of the mixed venous oxygen saturation are known, then the system of equations can be solved.

If the value of K is known or estimated, then the system of Equations 20A and 20B can be solved and CO and $S_LO_{2(1)}$ calculated.

However, it is recognized that the mathematical modeling of errors from uncertainty of the venous oxygen saturation will change in response to the decrease in arterial oxygen saturation.

The errors produced by any unknown changes in venous oxygen saturation in response to the decrease in arterial oxygen saturation may be mathematically analyzed for two possible cases:

Case 1. Pre-oxygenator venous oxygen saturation is not available.

Case 2. Pre-oxygenator venous oxygen saturation is available.

Case 2, where the pre-oxygenator venous oxygen saturation is available, is related to ECMO devices that routinely measure the pre-oxygenator oxygen saturation $S_{VOX}O_2$. Also, in some clinics a blood sample is taken to measure pre-oxygenator venous oxygen saturation. A true value of oxygen saturation of venous blood in central vein $S_vO_{2(W)}$ can be estimated from the oxygen saturation of blood entering oxygenator 120 $S_{VOX}O_2\%$, if recirculation is known:

$$S_vO_{2(W)} = \frac{(S_{vox}O_2 - R\%)}{\left(1 - \frac{R\%}{100}\right)} \quad \text{Eq. 25}$$

While it is not certain how accurately oxygen saturation of withdrawn blood $SvO_{2(w)}$ represents the mixed $SvO_2$ in equation 21, its dynamic changes may help to make a choice for direction/magnitude of changes in K in Eq. 24.

Therefore, the controller can be configured to calculate cardiac output based upon equations 1 through 25; and in further configurations, the controller is configured to calculate cardiac output based upon equations 4, 9A, 11, 12, 12A, 19, 20A, 20B, 23 and 24.

It is understood the indicator is any substance that alters a measurable blood property. The indicator may alter any measurable parameter of the blood. For example, the indicator may be chemical, optical, electrical, thermal or any combination thereof. The particular indicator is at least partly dictated by the anticipated operating environment. Available indicators include saline solutions, increased or decreased temperature as well as dyes and various isotopes. The use of temperature differentials may be accomplished by locally creating a heat source (such as a heater in the oxygenator 120) or a heat sink in the surrounding flow. The creation of a local temperature gradient offers the benefit of being able to employ a dilution indicator without introducing any additional volume into the blood flow. That is, a temperature differential may be created without an accompanying introduction of a volume of indicator. Alternatively, a volume of heated or cooled blood may be introduced at the indicator introduction port 114 as the indicator. It is also contemplated, that a component of the extracorporeal circuit 100 can be controlled to create or induce an indicator within the flow in the extracorporeal circuit. For example, a filtration or treatment rate or heater can be sufficiently changed to create an effective indicator in the extracorporeal circuit 100 which then travels through the cardiopulmonary system 30.

For purposes of description, the term calculate (or calculating) means determine the amount or number of something mathematically, including to evaluate or estimate the nature, amount or quantity.

For purposes of description, the term measure (or measuring) means how much there is of the relevant parameter, including ascertain the size, amount, or degree of (something) such as by using an instrument or device marked in standard units or by comparing it with an object of known size, wherein the measuring may be of representative or a surrogate value or a surrogate parameter. For example, for measuring the oxygenated blood flow rate introduced into the patient circulation system 20, the setting of the pump 130 can be used, a separate flow meter can be used, or dilution measurement can be used. It is further contemplated that measuring can include a calculating step or steps.

As used herein, the term calculate or calculating means to discover or identify a number or an amount using mathematics, a mathematical processes or equations.

As used herein, the term surrogate is a parameter which is used as a metric for one or more other parameters. Therefore, for purposes of description, when a specific parameter is recited as measured, it is understood that such measurement includes a representative of the parameter or a surrogate parameter that is measured, without deviating from the present system. Thus, it is understood that measuring a blood flow, recirculation or oxygen saturation encompasses measuring the relevant representative parameter as well as measuring a surrogate parameter. For example, it is understood the oxygen content (which may include contribution from other portions of the blood such as the plasma) can be measured in place of arterial oxygen saturation. Although the present analysis is set forth in terms of oxygen saturation, it is intended that oxygen content can be employed and that the recited oxygen saturation encompasses oxygen saturation as well as oxygen content.

Although the present method and equations are set forth in terms of oxygen saturation, it is understood that other parameters and/or gases of the blood can be used in place of the blood oxygen saturation. That is, as soon as blood is pumped by the pump 130 in the extracorporeal circuit 100, there will be different physical/chemical property of the blood than the blood flowing in the veins. For example, if the blood is cooled (or heated) in the oxygenator 120, while the blood temperate flowing in the body is at body temperature, then upon measuring the temperature in the artery, the recorded temperature will be a mixture and the analogous concept of heat balance can be applied.

It is further contemplated that if the patient were also on a ventilator, a rate of respiration could be changed (decreased or even temporarily halted) to impart a change in a blood parameter to be measured corresponding to the respective blood flows.

Thus, in one configuration, the present system includes providing at least a first and a different second blood flow rate from the extracorporeal circuit 100 wherein a blood parameter is measured on the arterial side of the patient circulation system 20 during or corresponding to the first flow rate and during or corresponding the second flow rate, as well as a recirculation corresponding to each of the first and the second flow rates. As set forth above in the equations, these values can then be used to calculate CO.

This disclosure has been described in detail with particular reference to an embodiment, but it will be understood that variations and modifications can be effected within the spirit and scope of the disclosure. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method for calculating cardiac output of a patient undergoing veno-venous extracorporeal blood oxygenation, the method comprising:
    (a) establishing a first blood flow rate from an extracorporeal blood oxygenation circuit into a venous portion of a patient circulation system;
    (b) measuring the first blood flow rate;
    (c) measuring a first value of a blood parameter in a portion of the patient circulation system corresponding to the first blood flow rate;
    (d) measuring a first recirculation in the extracorporeal blood oxygenation circuit corresponding to the first blood flow rate;
    (e) establishing a second blood flow rate from the extracorporeal blood oxygenation circuit into the venous portion of a patient circulation system;
    (f) measuring the second blood flow rate;
    (g) measuring a second value of the blood parameter in the portion of the patient circulation system corresponding to the second blood flow rate;
    (h) measuring a second recirculation in the extracorporeal blood oxygenation circuit corresponding the second blood flow rate; and
    (i) calculating a cardiac output of the patient corresponding to the first blood flow rate, the second blood flow rate, the first value of the blood parameter, the second value of the blood parameter, the first recirculation and the second recirculation.

2. The method of claim 1, further comprising measuring the first value of the blood parameter during the first blood flow rate from the extracorporeal blood oxygenation circuit.

3. The method of claim 1, further comprising operably connecting a first dilution sensor to the extracorporeal circuit for measuring one of the first recirculation and the second recirculation.

4. The method of claim 1, wherein the blood parameter is an arterial oxygen saturation of the patient.

5. The method of claim 1, wherein measuring the first value of the blood parameter includes measuring the first value of the blood parameter in an arterial portion of the patient.

6. The method of claim 1, wherein one of measuring the first blood flow rate; measuring the first value of the blood parameter; measuring the first recirculation; measuring the second blood flow rate; measuring the second value of the blood parameter; and measuring the second recirculation includes measuring a surrogate parameter.

7. The method of claim 1, further comprising adjusting the calculated cardiac output by an amount corresponding to one of an oxygen saturation of mixed venous blood after passing the lungs and the oxygenation saturation of the blood in the extracorporeal circuit prior to passing an oxygenator in the extracorporeal circuit corresponding to at least one of the measured first blood flow rate and the measured second blood flow rate.

8. A method for calculating cardiac output of a patient undergoing veno-venous extracorporeal oxygenation, the method comprising:
  (a) withdrawing blood from a first venous portion of a patient circulation system to pass the withdrawn blood into a veno-venous extracorporeal circuit, the veno-venous extracorporeal circuit having an access line, a return line and a blood oxygenator intermediate the access line and the return line, such that the withdrawn blood enters the extracorporeal circuit through the access line and is returned to the patient through the return line;
  (b) passing the withdrawn blood through the access line and the blood oxygenator to form oxygenated blood;
  (c) passing the oxygenated blood from the oxygenator and through the return line;
  (d) introducing the oxygenated blood from the return line to a second venous portion of the patient circulation system;
  (e) measuring a first blood flow rate through the extracorporeal circuit;
  (f) measuring an arterial oxygen saturation of the patient;
  (g) measuring a venous oxygen saturation of the patient; and
  (h) calculating a cardiac output of the patient corresponding to the measured first blood flow rate, the measured arterial oxygen saturation and the measured venous oxygen saturation.

9. The method of claim 8, wherein the first blood flow rate is measured by indicator dilution.

10. The method of claim 8, wherein measuring the arterial oxygen saturation includes measuring the arterial oxygen saturation by a pulse oximeter.

11. The method of claim 8, further comprising measuring an amount of recirculation and adjusting the calculated cardiac output corresponding to the amount of recirculation.

12. The method of claim 8, wherein the first venous portion and the second venous portion are different.

13. The method of claim 8, wherein the first venous portion and the second venous portion are coextensive.

14. The method of claim 8, wherein measuring a first blood flow rate through the extracorporeal circuit includes measuring a blood flow rate in at least one of the access line, the blood oxygenator and the return line.

15. The method of claim 8, wherein at least one of measuring the first blood flow rate, measuring the arterial oxygen saturation and measuring the venous oxygen saturation includes measuring a surrogate parameter.

16. The method of claim 8, wherein passing the withdrawn blood includes pumping the withdrawn blood.

17. The method of claim 8, further comprising adjusting the calculated cardiac output by an amount corresponding to an oxygen saturation of mixed venous blood after passing the lungs and an amount of recirculation of oxygenated blood withdrawn into the extracorporeal circuit prior to passing through a cardiopulmonary system of the patient.

18. A method for calculating cardiac output of a patient undergoing veno-venous extracorporeal blood oxygenation, the method comprising:
  (a) measuring a first arterial oxygen saturation corresponding to a first blood flow rate of oxygenated blood delivered to a venous portion of a patient circulation system by an extracorporeal blood oxygenation circuit;
  (b) measuring a second arterial oxygen saturation corresponding to a second blood flow rate of oxygenated blood delivered to the venous portion of the patient circulation system by the extracorporeal blood oxygenation circuit; and
  (c) adjusting a value of a calculated cardiac output by an amount corresponding to a difference between the first measured arterial oxygen saturation and the second measured arterial oxygen saturation, wherein the calculated value of cardiac output is based on the first measured arterial oxygen saturation; the second measured arterial oxygen saturation; the first blood flow rate and the second blood flow rate.

19. The method of claim 18, further comprising calculating the value of the cardiac output corresponding to a first measured recirculation during the first blood flow rate and a second measured recirculation during the second blood flow rate.

20. The method of claim 18, wherein adjusting the value of the cardiac output by the amount includes adjusting the value of the cardiac output by the amount proportional to the difference between the first measured arterial oxygen saturation and the second measured arterial oxygen saturation.

* * * * *